United States Patent
Papin et al.

(10) Patent No.: US 10,907,122 B2
(45) Date of Patent: Feb. 2, 2021

(54) OPTICAL DENSITY SYSTEM AND RELATED METHOD THEREOF

(71) Applicant: University of Virginia Patent Foundation, Charlottesville, VA (US)

(72) Inventors: Jason A. Papin, Charlottesville, VA (US); Bonnie V. Dougherty, Charlottesville, VA (US); Alisha Mae Geldert, Berkeley, CA (US); Kevin P. Seitter, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 385 days.

(21) Appl. No.: 15/569,195

(22) PCT Filed: Apr. 29, 2016

(86) PCT No.: PCT/US2016/030206
§ 371 (c)(1),
(2) Date: Oct. 25, 2017

(87) PCT Pub. No.: WO2016/176622
PCT Pub. Date: Nov. 3, 2016

(65) Prior Publication Data
US 2018/0105779 A1    Apr. 19, 2018

Related U.S. Application Data

(60) Provisional application No. 62/154,332, filed on Apr. 29, 2015.

(51) Int. Cl.
*G01N 21/59* (2006.01)
*G01N 21/51* (2006.01)
(Continued)

(52) U.S. Cl.
CPC .......... *C12M 1/3453* (2013.01); *C12M 23/08* (2013.01); *C12M 41/30* (2013.01);
(Continued)

(58) Field of Classification Search
CPC .... C12M 1/3453; C12M 23/08; C12M 41/30; C12M 41/36; C12M 41/46; C12M 41/00;
(Continued)

(56) References Cited

U.S. PATENT DOCUMENTS 5,697,373 A * 12/1997 Richards-Kortum ...................... A61B 5/0071
356/301
6,095,982 A   8/2000 Richards-Kortum
(Continued)

FOREIGN PATENT DOCUMENTS

DE  102014001284   1/2015
WO  WO 2006/117191  11/2006
(Continued)

OTHER PUBLICATIONS

Cox et al., "Continuous turbidometric measurements of microbial cell density in bioreactors using a light-emitting diode and a photodiode", Journal of Microbiological Methods, 1989, pp. 25-31, vol. 10, No. 1.
(Continued)

*Primary Examiner* — Brian J. Sines
(74) *Attorney, Agent, or Firm* — Robert J. Decker

(57) ABSTRACT

An apparatus and related method for determining the optical density and/or change in optical density of a reaction mixture in an agitated vessel or container. The apparatus may include at least one electromagnetic emitter configured to pass radiation through the reaction mixture to at least one receptor, whereby the receptor receives the transmitted or scattered light, while the reaction mixture is subjected to
(Continued)

shaking. The emitters may have an interchangeable association with the vessel or container and/or the receptors may have an interchangeable association with the vessel or container. Further, a processor may be provided to receive the transmitted or scattered light data and filter to eliminate or reduce the effect of the frequency at which the reaction mixture is shaken. The processor analyzes the filtered data to provide the optical density and/or change in optical density of the reaction mixture.

47 Claims, 9 Drawing Sheets

(51) Int. Cl.
*G01N 21/00* (2006.01)
*G01N 21/75* (2006.01)
*C12M 1/34* (2006.01)
*C12M 1/24* (2006.01)
*G01N 21/17* (2006.01)

(52) U.S. Cl.
CPC ............ *C12M 41/36* (2013.01); *C12M 41/46* (2013.01); *G01N 21/1717* (2013.01); *G01N 21/51* (2013.01); *G01N 21/59* (2013.01); *G01N 2021/1744* (2013.01)

(58) Field of Classification Search
CPC ... C12M 41/32; G01N 21/1717; G01N 21/51; G01N 21/59; G01N 2021/1744; G01N 21/00; G01N 21/75; G01N 15/06; G01N 33/00; G01N 33/48
See application file for complete search history.

(56) References Cited

U.S. PATENT DOCUMENTS

| | | | |
|---|---|---|---|
| 7,318,656 | B1 | 1/2008 | Merine |
| 7,339,671 | B2 | 3/2008 | Peng |
| 8,405,033 | B2 | 3/2013 | Debreczeny |
| 8,603,772 | B2 | 12/2013 | Debreczeny |
| 2012/0194800 | A1 | 8/2012 | Debreczeny |
| 2015/0260642 | A1 | 9/2015 | Papin |
| 2018/0011027 | A1* | 1/2018 | Herzog ................. G01N 21/51 |

FOREIGN PATENT DOCUMENTS

| | | |
|---|---|---|
| WO | WO 2007/001248 | 1/2007 |
| WO | WO 2014/058869 | 4/2014 |
| WO | WO 2015/050464 | 4/2015 |
| WO | WO 2015/114083 | 8/2015 |

OTHER PUBLICATIONS

Jensen et al., "Miniaturized Plate Readers for Low-Cost, High-Throughput Phenotypic Screening", Journal of Laboratory Automation, Epub Nov. 3, 2014, pp. 51-55, vol. 20, No. 1.

Monod, "The Growth of Bacterial Cultures", Annual Reviews in Microbiology, 1949, pp. 371-394, vol. 3, No. 1.

Myers et al., "Improving accuracy of cell and chromophore concentration measurements using optical density", BMC biophysics, 2013, 15 pages, vol. 6, No. 4.

Presens, SFR Shake Flask Reader, 2015, 4 pages, Systems PreSens Precision Sensing GmbH, found at: https://www.presens.de/products/detail/sfr-shake-flask-reader.html.

Sivashanmugam et al., "Practical protocols for production of very high yields of recombinant proteins using *Escherichia coli*", Protein Science, 2009, pp. 936-948, vol. 18, No. 5.

Toprak et al., "Building a morbidostat: an automated continuous-culture device for studying bacterial drug resistance under dynamically sustained drug inhibition", Nature Protocols, 2013, pp. 555-567, vol. 8, No. 3.

Udekwu et al., "Functional relationship between bacterial cell density and the efficacy of antibiotics", Journal of Antimicrobial Chemotherapy, 2009, pp. 745-757, vol. 63, No. 4.

Underwood et al., "Lack of Protective Osmolytes Limits Final Cell Density and Volumetric Productivity of Ethanologenic *Escherichia coli* KO11 during Xylose Fermentation", Applied and Environmental Microbiology, 2004, pp. 2734-2740, vol. 70, No. 5.

\* cited by examiner

OPTICAL DENSITY SYSTEM AND RELATED METHOD THEREOF

RELATED APPLICATIONS

The present application is a national stage filing of International Application No. PCT/US2016/030206, filed Apr. 29, 2016, which claims benefit of priority under 35 U.S.C § 119 (e) from U.S. Provisional Application Ser. No. 62/154,332, filed Apr. 29, 2015, entitled "Optical Density System and Related Method Thereof;" the disclosures of which are hereby incorporated by reference herein in their entirety.

FIELD OF THE INVENTION

The present invention relates generally to methods and devices for measuring the optical density of a mixture in a vessel or container. More specifically, the invention measures the optical density of mixtures in a shaken or agitated reactor.

BACKGROUND

Optical density (OD) is a standard indicator of bacterial concentration, which is commonly measured during bacterial growth experiments. These growth measurements are essential in a wide range of applications, including antibiotic testing, genetic engineering, and protein production. Bacterial concentration must be measured frequently to obtain sufficient temporal resolution to distinguish rapidly changing growth phases. Previously, researchers needed to obtain a separate culture sample and place it in a spectrophotometer for each OD measurement, which makes frequent measurements very time- and resource-intensive. Researchers conservatively estimate that 30% of a bacterial growth experiment (which can last over 10 hours) is spent manually collecting measurements. Furthermore, frequent sampling also increases the risk of contamination, requires cultures to be repeatedly removed from controlled environments such as an incubator, and generates many discarded materials. Researchers therefore desire a low-cost way to measure OD automatically from standard bacterial culture flasks in a shaker-incubator.

In general, the state of the art for automatic measurements of OD in culture flasks includes measuring OD with LED-photodetector pairs as opposed to the purely monochromatic light sources that are used in standard spectrophotometers; both scattering-based and transmission-based approaches have been used. Many attempts to employ these techniques, however, require the culture to be flowed through a separate compartment around which an emitter-detector pair is placed, which precludes the culture from being grown in standard laboratory containers and results in a larger, more complicated device. Attempts to overcome this limitation have been largely limited to static vessels or containers.

One such attempt is an OD measurement technique comprising holding an OD scanner up to the flask surface while tilting the flask, if necessary, to accumulate sufficient liquid near the sensor. Consisting of a handheld OD scanner, this method requires user intervention and therefore, precludes continuous OD measurement. With both the emitters and receptors on the same side of the reaction mixture, the method relies on scattered-light measurements. The method is therefore further limited to instances in which the container or vessel contains a significant accumulation of the reaction mixture, requiring alteration of testing protocols.

Another disclosed method of OD measurement includes mounting the measurement apparatus on the side of the container or flask to provide continuous OD measurements. Also comprising emitters and receptors placed on the same side of the reaction mixture, this method is similarly limited to instances in which the container or vessel contains a significant accumulation of the reaction mixture in close proximity to the emitter and receptor assembly. In an agitated vessel or container, however the accumulation of the reaction mixture on one side of the vessel or container will be inconsistent, thereby creating distortion in the OD measurements. This distortion precludes application of this method to agitated or shaken vessels or containers.

In general, methods of continuous measurement of shaken or agitated vessels or containers require expensive and specialized flasks and measure only oxygen content and pH of flask cultures. Attempts to continuously measure the OD of a shaken or agitated vessel or container are generally limited and inflexible in application. One method requires that the shaking occur at a frequency that is not an integer multiple of the measurement frequency, thereby limiting the operable relationship between the shaking frequency and the measurement frequency. To achieve this, the corresponding algorithm demands significant computational power and therefore, requires a larger device or apparatus. The device is further limited to conducting measurements at a single set of parameters, including wavelength and vessel or container size, as the emitters and receptors are fixed to the measurement apparatus.

More recently, the present Applicant provided an automated device to measure OD from bacterial samples growing in a 96-well plate, but it can only measure OD from well plates, not flasks. However, many researchers are hesitant to culture bacteria in well plates rather than flasks because of possible differences in oxygenation and temperature control, as well as the increased cost over time of disposable plates.

In view of the above, a need arises to provide a reliable OD measurement of a mixture in an agitated vessel or container, capable of use with standard laboratory containers.

In view of the above, a need arises for automated and real-time and/or continuous OD measurements of a mixture in an agitated vessel or container, capable of use with standard laboratory containers.

Overview

In various aspects, an embodiment of the current invention comprises a radiation sensing technique for measuring the OD and particle concentration for a shaken or agitated vessel or container. This technique accurately tracks bacterial growth with no required human intervention, can be used in existing shaking-incubators with little or no modification, and is compatible with standard Erlenmeyer flasks in a wide range of sizes.

According to an aspect of an embodiment of the invention, the method for determining the optical density and/or change in optical density of a reaction mixture in an agitated vessel or container comprises: passing radiation through the mixture from at least one electromagnetic emitter to at least one receptor; receiving the radiation passed through the reaction mixture with at least one receptor; measuring the transmitted or scattered light detected by said at least one receptor; shaking said vessel or container and said reaction mixture during said measurement of the transmitted or scattered light; passing the raw measurement through a frequency filter of predetermined width to eliminate or reduce the effect of the frequency of the shaken reaction mixture; and analyzing the filtered data to provide the optical density and/or change in optical density of said reaction mixture. In utilizing a filter of predetermined width, the method is capable of mitigating the effect of the shaking and thus, extracting a robust measurement of the optical density of the reaction mixture over several periods of shaking. Further, applying a frequency filter of predetermined width the method allows the filtering parameters to be tailored and applied to various testing protocols prior to commencing the procedure without the need to subsequently control the frequency of the detection and/or the frequency of shaking. Similarly, the nature of the frequency filter requires less computational power thereby allowing for a smaller apparatus.

As disclosed, the apparatus for determining the optical density and/or change in optical density of a reaction mixture in an agitated vessel or container comprises: at least one electromagnetic emitter configured to pass radiation through the reaction mixture to at least one receptor, said at least one receptor configured to receive the transmitted or scattered light, while the reaction mixture is subjected to shaking; a processor configured to receive the transmitted or scattered light data, wherein said received data is passed through a frequency filter of predetermined width to eliminate or reduce the effect of the frequency at which the reaction mixture is shaken; and said processor configured to analyze the filtered data to provide the optical density and/or change in optical density of said reaction mixture.

Additionally, an aspect of an embodiment of the present invention discloses an apparatus for determining the optical density and/or change in optical density of a reaction mixture in an agitated vessel or container, said apparatus comprising: at least one electromagnetic emitter configured to pass radiation through the reaction mixture to at least one receptor, said at least one receptor configured to receive the transmitted or scattered light, while the reaction mixture is subjected to shaking; wherein: said at least one emitter is configured to be in interchangeable association with said vessel or container; said at least one receptor is configured to be in interchangeable association with said vessel or container; or said at least one emitter is configured to be in interchangeable association with said vessel or container, and said at least one receptor is configured to be in interchangeable association with said vessel or container; a processor configured to receive the transmitted or scattered light data and filter to eliminate or reduce the effect of the frequency at which the reaction mixture is shaken; and said processor configured to analyze the filtered data to provide the optical density and/or change in optical density of said reaction mixture.

Further, an aspect of an embodiment of the present invention includes an apparatus for determining the optical density and/or change in optical density of a reaction mixture in an agitated vessel or container, said apparatus comprising: at least one electromagnetic emitter configured to pass radiation through the reaction mixture to at least one receptor, said at least one receptor configured to receive the transmitted or scattered light, while the reaction mixture is subjected to shaking; wherein: said at least one emitter is configured to be in interchangeable association with said vessel or container; said at least one receptor is configured to be in interchangeable association with said vessel or container; or said at least one emitter is configured to be in interchangeable association with said vessel or container, and said at least one receptor is configured to be in interchangeable association with said vessel or container; a processor configured to receive the transmitted or scattered light data; and said processor configured to analyze the filtered data to provide the optical density and/or change in optical density of said reaction mixture.

In an embodiment of the disclosed present invention, the emitters and receptors are located on opposite sides of the reaction mixture. In a related embodiment, the emitters are disposed on the stopper and the receptors are disposed on the base assembly. This arrangement of emitters and receptors enables the apparatus to utilize transmission-based measurements and therefore, accommodate small quantities of the reaction mixture. Such a feature enables compatibility with a wider range of standard testing protocols.

Further, in an embodiment of the present invention, the components are in interchangeable association with the vessel or container. As such, emitters of different parameters and wavelengths can be interchangeably utilized with the same vessel or container and reaction mixture. By including multiple wavelengths in one device, fluorescence could be induced with an LED at the excitation wavelength, and then monitored with a photodetector at the emission wavelength. Similarly, the modularity of the components allows receptors of different parameters to be interchangeably utilized with the same vessel or container and reaction mixture. The modular, noninvasive design and continuous optical monitoring capabilities of the flask reader make it suitable for a wide range of applications.

The present inventors' evidence suggests that, in an embodiment but not limited thereto, the flask reader can read accurately and reproducibly from cultures shaking at up to at least 180 RPM, while taking measurements several times per second. Similarly, the present inventors' evidence suggests that, in an embodiment but not limited thereto, the flask reader can read accurately and reproducibly from cultures shaking at up to at least 180 RPM, while taking measurements every 7 milliseconds. This unprecedented temporal resolution eliminates the need for manual sampling, decreasing contamination risk, culture disturbance, volume depletion, and waste generation. Furthermore, an aspect of an embodiment of the present invention system and related method achieves these benefits without substantial change to the culturing environment, and is compatible with standard protocols, including incubation, shaking, and aeration (or lack thereof). The various benefits over existing technology with compatibility with existing protocols suggest that an embodiment of the present invention flask reader will be a highly impactful device in the field of bacterial research.

However, the present inventors submit that the potential applications of the flask reader extend beyond bacterial research to many situations in which optical properties must be continuously monitored. For example, an embodiment of the present invention flask reader could be used to monitor cell density or growth rate in industrial fermentation processes. Additionally, an embodiment would also be useful in enzyme assays to monitor the depletion of a certain substrate or generation of another. If none of the reactants or products absorb a specific wavelength, the process could be coupled to another reaction that can be optically monitored. Further, an embodiment pertaining to the continuous OD monitoring can also be used to assess homogeneity. For instance, by measuring the time it takes for a sample to reach a steady OD after addition of a substance, the diffusion, dissolution, or homogenization time can be measured. Moreover, the OD could then be used to quantify the degree of sample homogenization, to more precisely control it in experiments.

An aspect of an embodiment of the present invention provides, among other things, a method for determining the optical density and/or change in optical density of a reaction mixture in an agitated vessel or container. The method may comprise: passing radiation through the mixture; receiving the radiation passed through the reaction mixture; measuring the transmitted or scattered light that was received; shaking said vessel or container and said reaction mixture during said measurement of the transmitted or scattered light; passing the raw measurement through a frequency filter to eliminate or reduce the effect of the frequency of the shaken reaction mixture; and analyzing the filtered data to provide the optical density and/or change in optical density of said reaction mixture.

An aspect of various embodiments of the present invention apparatus and method for determining the optical density and/or change in optical density of a reaction mixture in an agitated vessel or container provides an automated and real-time and/or continuous OD measurement.

In an embodiment, the optical density and/or change in optical density of the reaction mixture may be provided to an output device. The output device may include, but not limited thereto, any one or more combination of the following: storage, memory, network, printer, or a display. Such output devices and related components may be local or remote, or some combination thereof.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Turning now to the drawings, the invention comprises various methods and apparatuses to more accurately measure the OD of a reaction mixture in a shaken or agitated vessel or container. An aspect of an embodiment of the present invention provides, but is not limited thereto, a system and method for monitoring long-term growth of flask-based shaken bacteria cultures. These growth measurements are essential in a wide range of applications, including antibiotic testing, genetic engineering, and protein production.

The present invention measures OD with at least one electromagnetic emitter (e.g., LED) and at least one receptor (e.g., photo detector); both scattering-based and transmission-based approaches have been used. As depicted in FIGS. 1-5, 8, 11, and 14, an aspect of an embodiment of the present invention includes at least one electromagnetic emitter 13, at least one receptor 17, and a vessel or container 11, which is configured for use with a reaction mixture 5.

Figure 1:
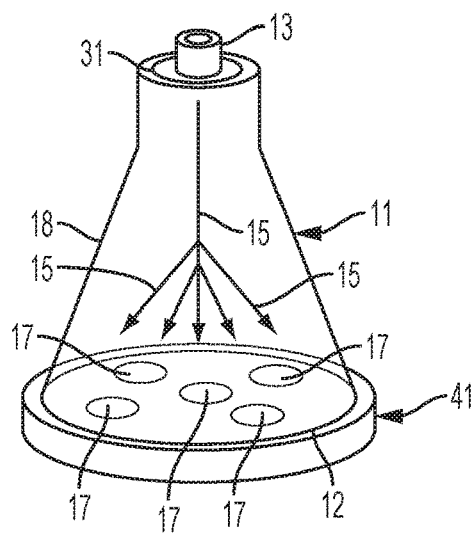
FIG. 1 is a perspective view of an aspect of an embodiment of the apparatus according to the present disclosure.
Figure 2:
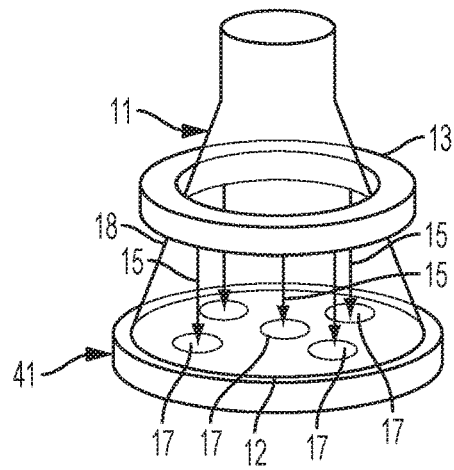
FIG. 2 is a perspective view of an aspect of an embodiment of the apparatus according to the present disclosure.
Figure 3:
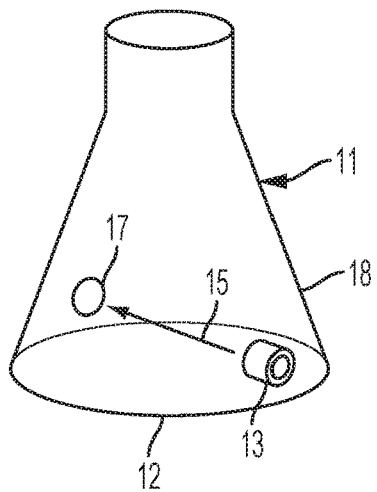
FIG. 3 is a perspective view of an aspect of an embodiment of the apparatus according to the present disclosure.
Figure 4:
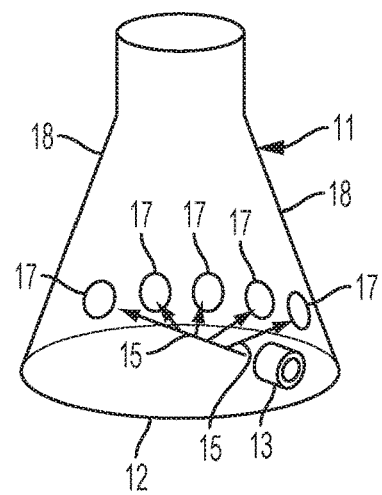
FIG. 4 is a perspective view of an aspect of an embodiment of the apparatus according to the present disclosure.
Figure 5:
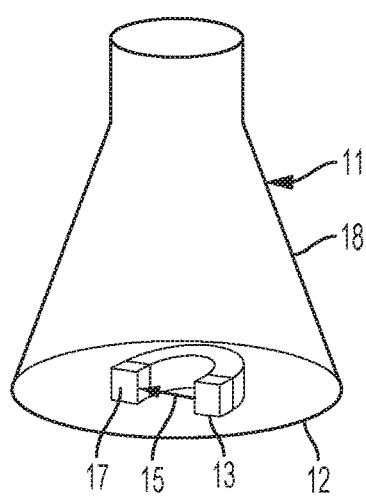
FIG. 5 is a perspective view of an aspect of an embodiment of the apparatus according to the present disclosure.

The number and position of the at least one emitter 13 and at least one receptor 17 with respect to the vessel or container 11 varies among embodiments. In general, the emitters 13 and receptors 17 can be arranged, but not limited thereto, with respect to the vessel or container 11 in the manner presented in FIGS. 1-5. With the emitters 13 and receptors 17 located opposite one another, these embodiments operate using a transmission-based measurement technique. FIGS. 2, 3, and 5 depict radiation 15 that is directly transmitted while the radiation 15 measured by the receptors in FIGS. 1 and 4 is both scattered and directly transmitted. By virtue of employing a transmission-based approach, the apparatus is capable of operating with small quantities of reaction mixtures present in the vessel or container as depicted, for example but not limited thereto, in FIGS. 11 and 14.

While the vessel or container 11 is shaken or agitated, radiation 15 is passed from at least one electromagnetic emitter 13 through the reaction mixture 5 to at least one receptor 17. In FIGS. 1 and 2, the radiation 15 is passed vertically through the reaction mixture to a plurality of receptors 17. Further, as depicted in these embodiments, the receptors 17 are located on a base 41 upon which the bottom 12 of the vessel or container 11 is disposed. In further embodiments, the association between vessel or container 11 and the base 41 is interchangeable, as the vessel or container 11 can be removed and another vessel or container can be disposed on said base. In FIG. 1, the least one emitter 13 is disposed upon a stopper 31. In another embodiment, depicted by FIG. 2, the at least one emitter 13 is configured in a ring around the perimeter of the vessel of container 11.

In FIGS. 3, 4, and 5, the radiation 15 is passed horizontally through the reaction mixture. FIGS. 3 and 4 depict the emitter 13 positioned on the side 18 of the vessel or container 11 (or mounted in communication with the side wall). FIG. 4 further depicts an embodiment wherein a plurality of receptors 17 is disposed in spaced relation on the side 18 of the vessel or container 11. In FIG. 3, the emitter 13 and receptor 17 are disposed in a pair on opposite sides 18 of the vessel or container 11. In FIG. 5, the emitter 13 and receptor 17 are disposed opposite one another inside the vessel or container 11. Further, in the depicted embodiment, the emitter 13 and receptor 17 are disposed on the bottom 12 of the vessel or container 11.

The at least one receptor 17 converts the received light data into raw measurement data in the form of an electric signal. In an example, the detection of the emitted radiation 15 by at said least one receptor 17 is effected at a substantially greater frequency than the frequency at which the vessel or container 11 is shaken. In so doing, the receptors 17 return several raw measurement data points for each shaking period, thereby enabling identification and mitigation of the signal distortion due to shaking. Furthermore, the method produces a reliable and robust result, as the measurements can be compared for several data points for each of the several shaking periods over which measurements are taken.

In order to achieve accurate readings despite the shaking of the vessel or container 11, the raw measurement data is post-processed using a frequency filter of pre-determined width. Said frequency filter of predetermined width may comprise, but is not limited to, a Gaussian moving average window to reduce the sidelobes in the resulting output signal. In one embodiment, the Gaussian moving average window width is selected to be 5.6 seconds. The Gaussian moving average window width in another embodiment is approximately five periods at the lowest shaking speed of the vessel or container 11. In yet another embodiment, the Gaussian moving average window length allows for approximately 800 measurements.

In an example, the raw data from each receptor 17 is passed through the frequency filter individually. The filtered data from each receptor 17 is then compared to select the curve with the smoothest output curve. In general, the filtered data is analyzed to provide the optical density of the reaction mixture 5 using Beer-Lambert's law, which is expressed as:

$$OD = -\log_{10}(I/I_0) \tag{Equation 1}$$

where ($I_0$) represents the reference intensity of the radiation and (I) represents the intensity of the radiation measured after transmission through the sample.

Figure 8:
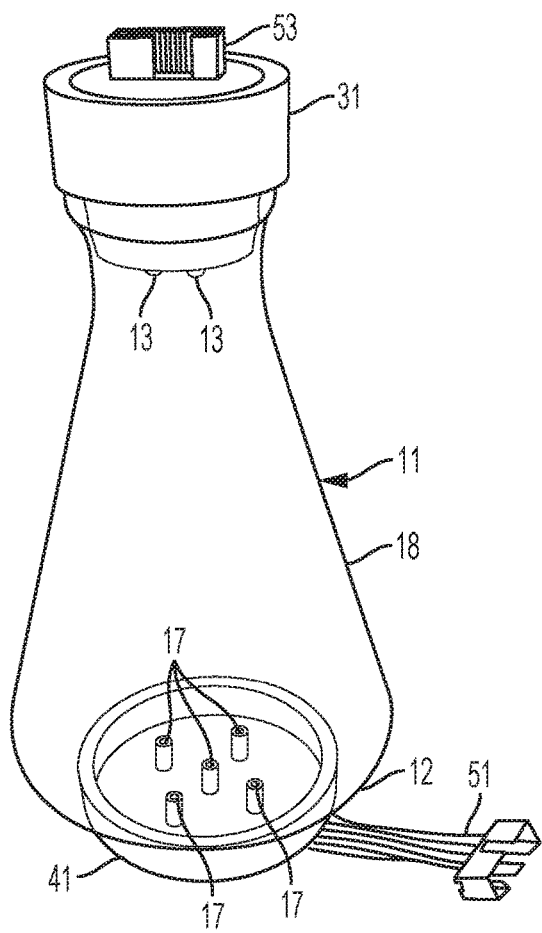
FIG. 8 is a perspective view of an aspect of an embodiment of the apparatus according to the present disclosure.

An aspect of an embodiment of the present invention is depicted in perspective view in FIG. 8. The apparatus comprises: at least one electromagnetic emitter 13 configured to pass radiation through the reaction mixture to at least one receptor 17, said at least one receptor configured to receive the transmitted or scattered light 15, while the reaction mixture 5 is subjected to shaking; a processor configured to receive the transmitted or scattered light 15 data, wherein said received data is passed through a frequency filter of predetermined width to eliminate or reduce the effect of the frequency at which the reaction mixture is shaken; and said processor configured to analyze the filtered data to provide the optical density and/or change in optical density of said reaction mixture. This embodiment is made compatible with the processor via communication lines 51 and a communication port 53. In an alternative embodiment, the processor and supporting hardware and firmware (electronics) may be self-contained locally at the flask such as in a base 41 or stopper 31, as well as in other related components as desired or required. Alternatively, the processor module (function) may be disposed locally as well remotely.

In an embodiment, the optical density and/or change in optical density of the reaction mixture may be provided to an output device. The output device may include, but not limited thereto, any one or more combination of the following: storage, memory, network, printer, or a display. Such output devices and related components may be local or remote, or some combination thereof.

The at least one electromagnetic emitter 13 are each operable to emit electromagnetic radiation along an optical path. In an example, the electromagnetic emitter 13 comprises an infrared light emitting diode. In other examples, the infrared light emitting diode comprises a peak emission between about 700 and 1000 nanometers ("nm"). In yet other examples, the electromagnetic emitter 13 comprises a visible light emitting diode. In further examples, the visible light emitting diode comprises a peak emission between 400 and 700 nm.

Figure 6:
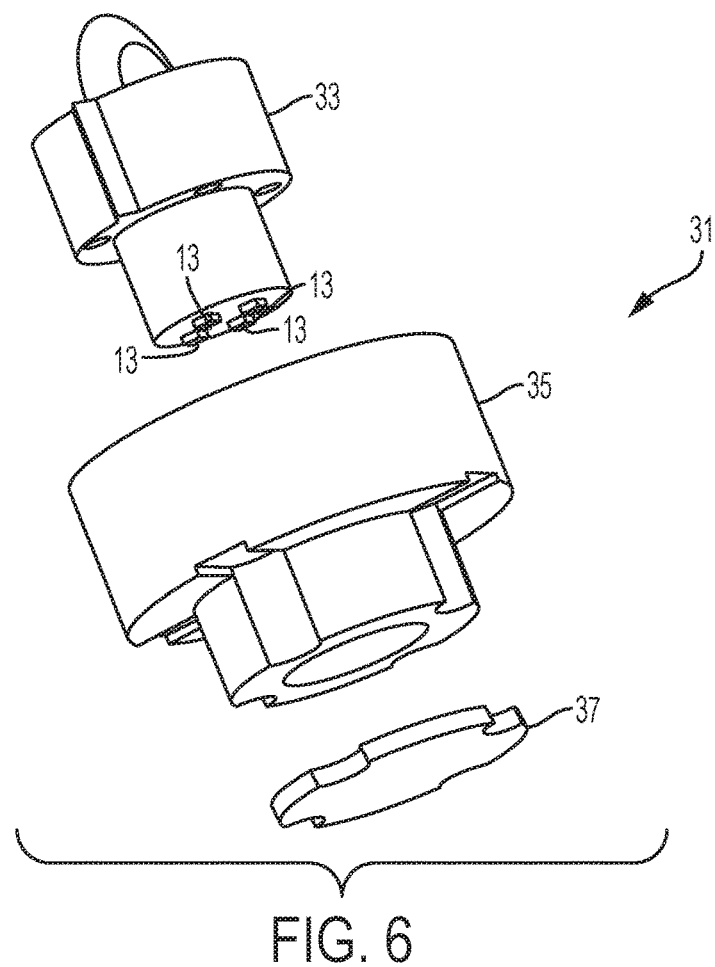
FIG. 6 is a partially exploded view of an aspect of an embodiment of the fluted stopper according to the present disclosure.
Figure 9:
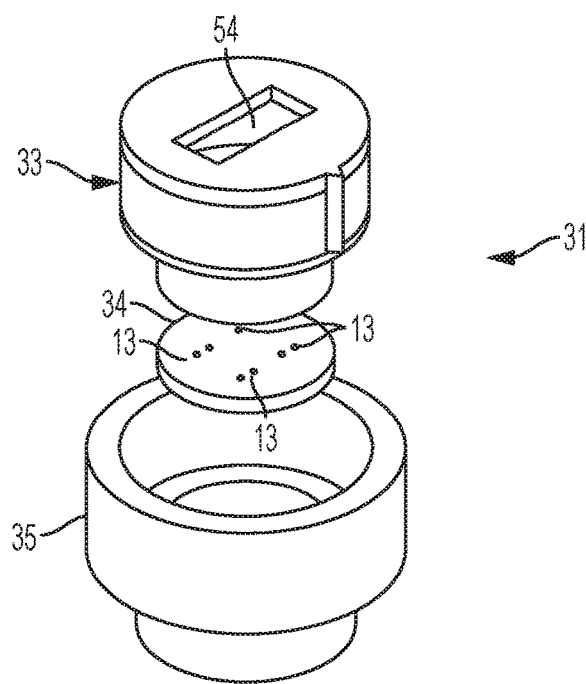
FIG. 9 is a partially exploded view of an aspect of an embodiment of the non-fluted stopper.

In an example, the emitters 13 are configured to be in interchangeable association with said vessel or container 11. In a further embodiment, the interchangeable association is provided by a stopper 31, wherein said stopper 31 comprises an inner stopper 33 and an outer stopper 35 as depicted in FIGS. 6 and 9. Because the stopper 31 has an interchangeable inner stopper 33, the apparatus allows a user to substitute emitters 13 of varying wavelengths disposed on different inner stoppers 33. Such modularity enables measurements at different wavelengths for different functionality, including but not limited to, monitoring fluorescence or the production of certain pigments.

The modularity further enables separate manufacturing of the inner stopper 33 and outer stopper 35. Therefore, the outer stopper 35 is inexpensively and separately manufactured in different sizes. With the inner dimensions of the outer stopper 35 remaining constant, the inner stopper 33 can therefore be interchangeably utilized with vessels or containers 11 of varying size without requiring the manufacture of additional emitters 13 (as well as other electronic or hardware elements and components as desired or required) and inner stoppers 33. Such modularity enables compatibility with a greater variety of standard testing protocols regardless of the required size of the vessel or container 11.

Additionally, in an embodiment, the outer stopper 35 can be easily changed between a fluted design, as depicted in FIG. 6, and a non-fluted design, as depicted in FIG. 6. The fluted stopper 31 in FIG. 6 comprises a fluted outer stopper 35 and a fluted cover 37 for the inner stopper 31. Utilizing the same inner stopper 33 with the fluted and non-fluted embodiments allows for the method and apparatuses to be interchangeably utilized in testing procedures requiring different levels of oxygenation. FIG. 9 further depicts an aspect of an embodiment of the inner stopper 31 wherein the emitters 13 are disposed on the emitter surface 34 of the inner stopper 33.

Figure 7:
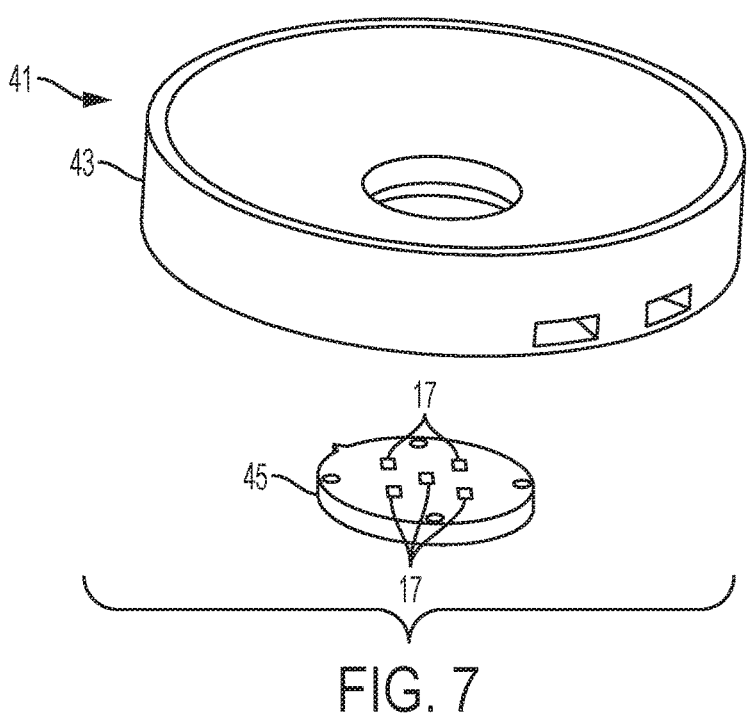
FIG. 7 is a partially exploded view of an aspect of an embodiment of the base.
Figure 10:
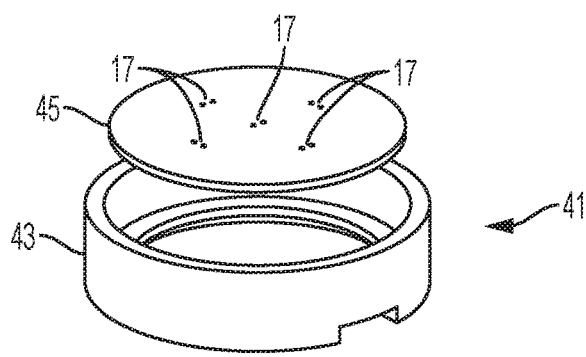
FIG. 10 is a partially exploded view of an aspect of an embodiment of the base.

In an embodiment, the base 41 is also interchangeably associated with vessel or container 11. FIG. 10 is a partially exploded view of an aspect of an embodiment of the base 41, comprising an inner base 45 and an outer base 43. The receptors 17 are disposed on the inner base 45 and are therefore in removable association with the vessel or container 11. The modularity of the base 41 enables the outer base 43 to be manufactured separately from the inner base 45 and receptors 17. Therefore, the outer base 43 is inexpensively and separately manufactured in different sizes. With the inner dimensions of the outer base 43 remaining constant, the inner base 45 can therefore be interchangeably utilized with vessels or containers 11 of varying size without requiring the manufacture of additional receptors 17 (as well as other electronic or hardware elements and components as desired or required) and inner bases 45. Such modularity enables compatibility with a greater variety of standard testing protocols regardless of the required size of the vessel or container 11. FIG. 7 depicts an aspect of a similar embodiment of the base 41 wherein the base 41 has a lip to support the container or vessel 11. This embodiment similarly possesses the modularity and accompanying advantages of the embodiment depicted in FIG. 10. Referring to FIGS. 7 and 10, the receptors 17 may be interchangeably disposed on said inner base 45 or disposed on any substrate associated with the inner base 45.

Figure 11:
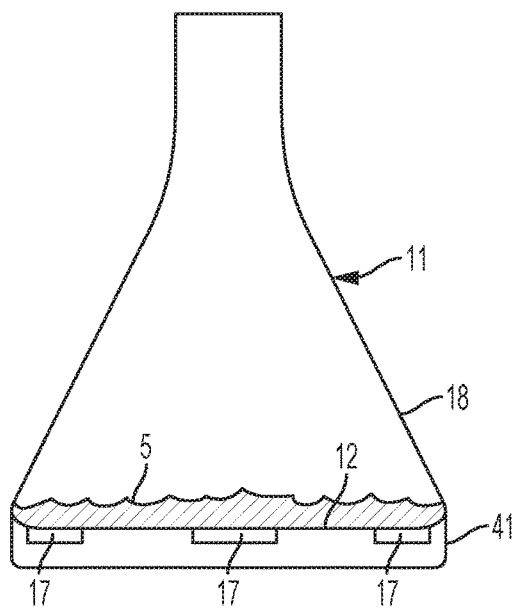
FIG. 11 is a side view of an aspect of an embodiment of the apparatus containing a reaction mixture according to the present disclosure.
Figure 14:
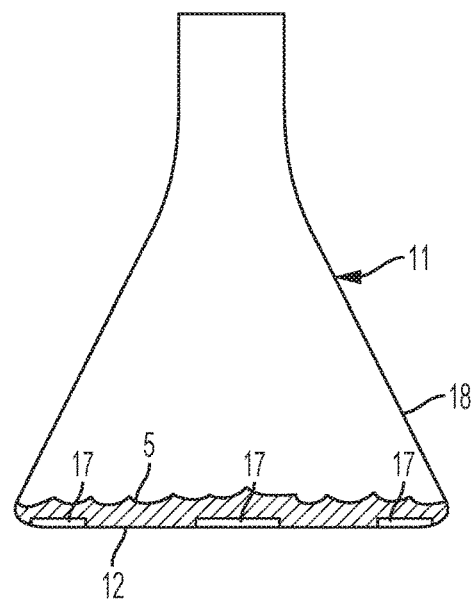
FIG. 14 is a side view of an aspect of an embodiment of the apparatus containing a reaction mixture according to the present disclosure.

FIGS. 11 and 14 depict side views of aspects of an embodiment of the apparatus containing a reaction mixture 5 according to the present disclosure. FIG. 11 depicts an embodiment wherein the receptors 17 are disposed on a base 41 with which the vessel or container 11 is interchangeably associated. In an alternative embodiment, as depicted in FIG. 14, the receptors are disposed on the bottom 12 of the vessel or container 11. As depicted in these drawings, the apparatuses and methods are capable of providing robust OD measurements even when only a small quantity of the reaction mixture 5 is present.

Figure 12:
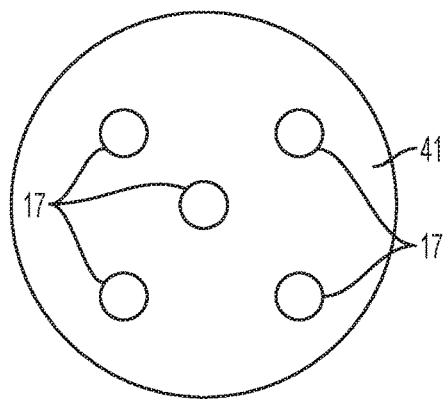
FIG. 12 is a top view of an aspect of an embodiment of the base comprising a plurality of receptors.
Figure 13:
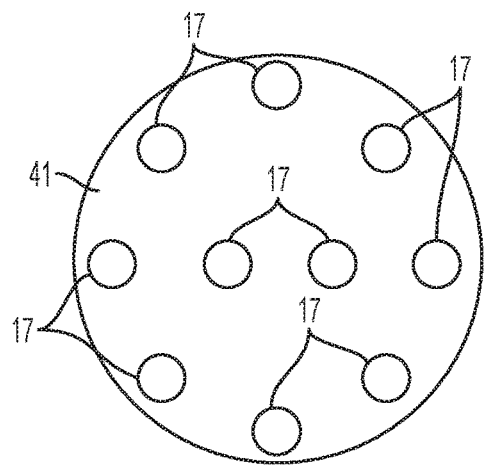
FIG. 13 is a top view of an aspect of an embodiment of the base comprising a plurality of receptors.
Figure 15:
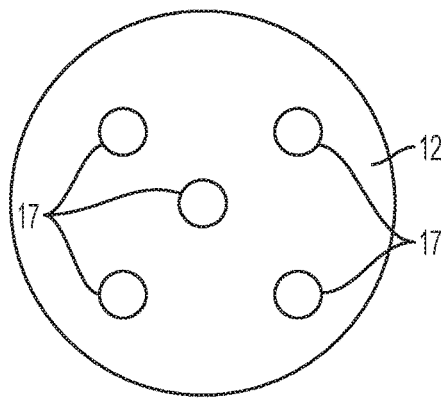
FIG. 15 is a top view of an aspect of an embodiment of the bottom of the vessel or container comprising a plurality of receptors.
Figure 16:
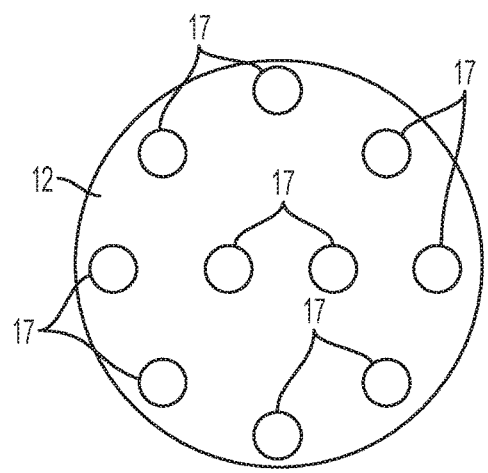
FIG. 16 is a top view of an aspect of an embodiment of the bottom of the vessel or container comprising a plurality of receptors.

As depicted in FIGS. 12 and 13, the number and position of the receptors 17 disposed on the base 41 varies among embodiment. Similarly, FIGS. 15, and 16 demonstrate that the number and position of the receptors disposed on the bottom 12 of the vessel or container varies among embodiments. In an example, depicted by FIG. 16, the receptors 17 are positioned proximal to or at the perimeter of the bottom 12 of the vessel or container 11. This positioning mitigates the impact of the frequency of the shaking, as the receptors 17 detect the radiation 15 transmitted through the reaction mixture 5 as it accumulates on the edges of the vessel or container 11 during shaking.

Figure 17:
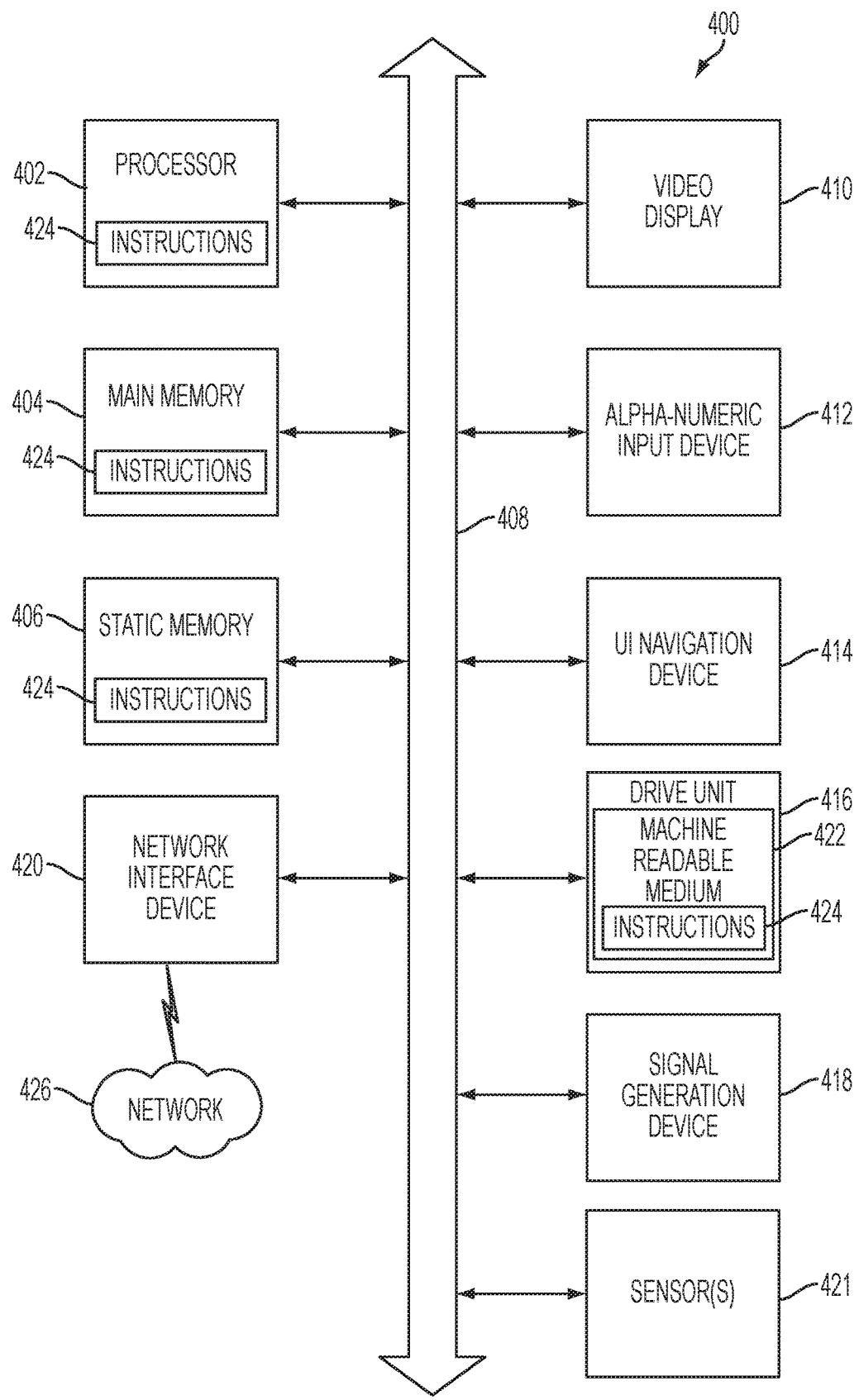
FIG. 17 is a block diagram illustrating an example of a machine upon which one or more aspects of embodiments of the present invention can be implemented.

FIG. 17 is a block diagram illustrating an example of a machine upon which one or more aspects of embodiments of the present invention can be implemented.

FIG. 17 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations. In an example, a circuit can be implemented mechanically or electronically.

For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a standalone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Figure 18:
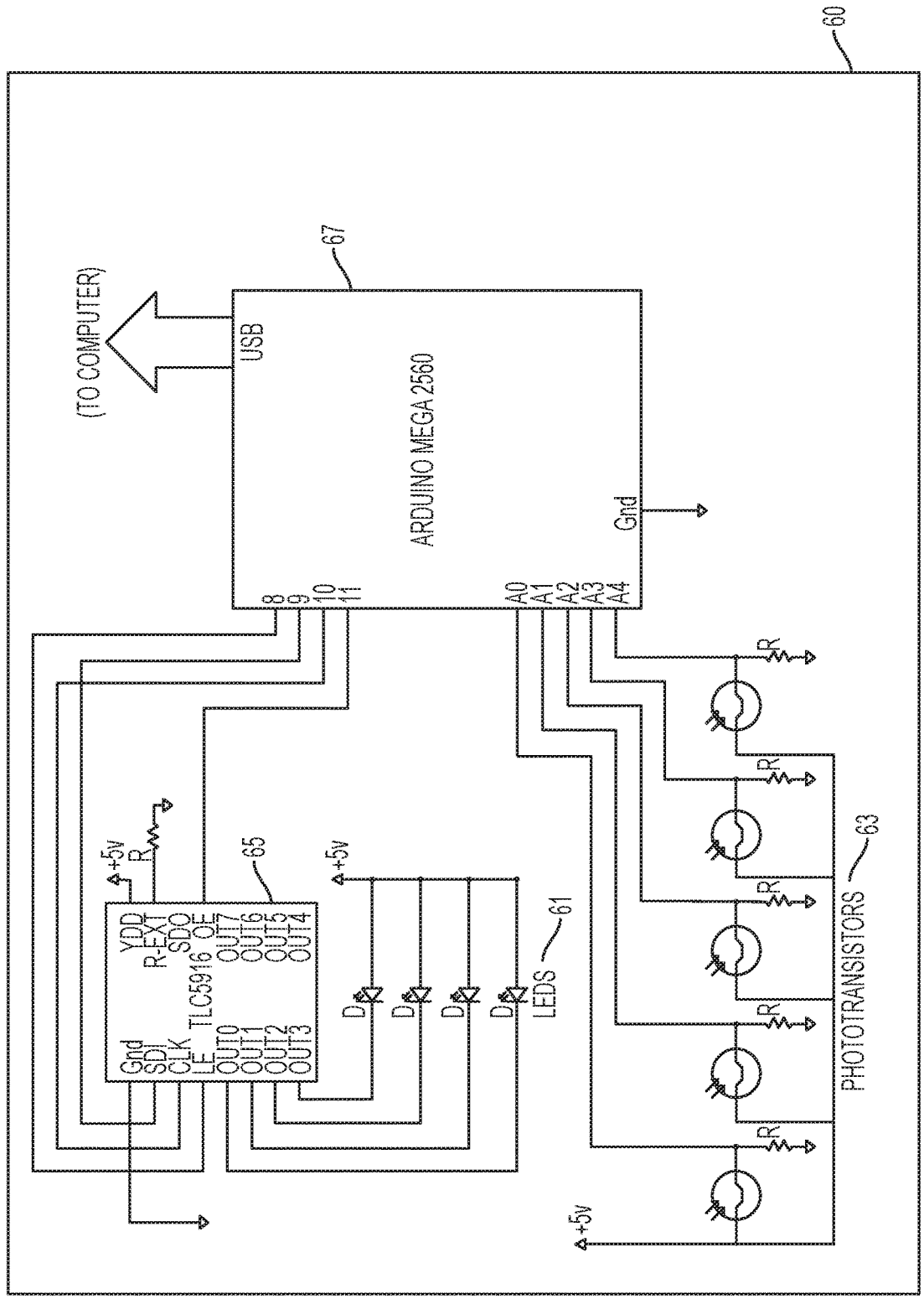
FIG. 18 is a schematic block diagram for a system or related method of an embodiment of the present invention in whole or in part.
Figure 19:
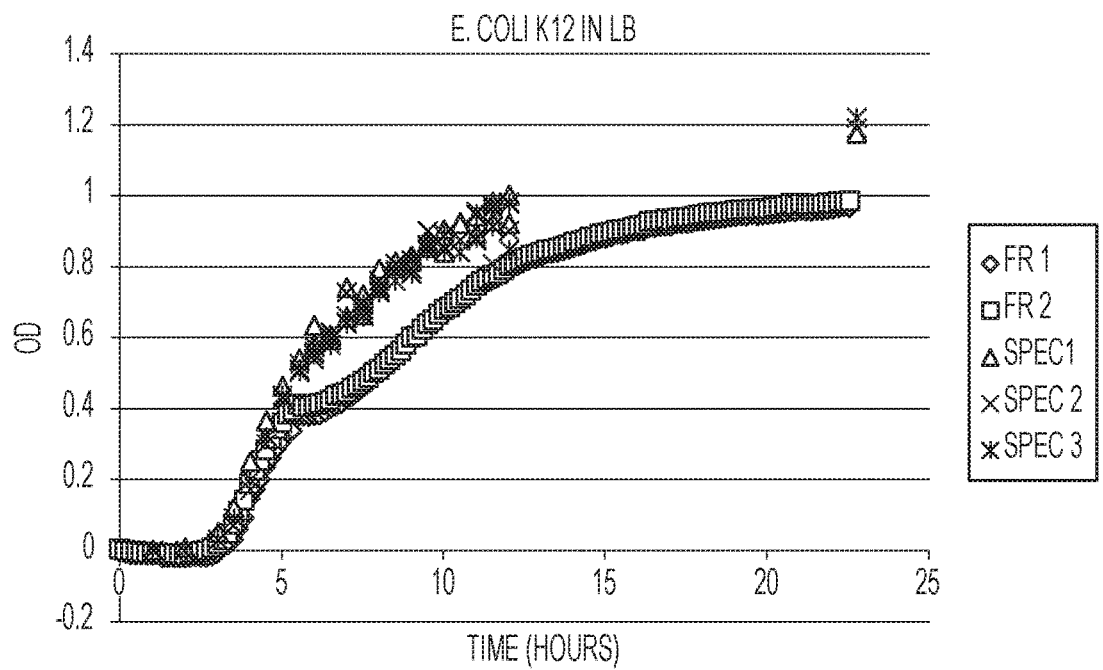
FIG. 19 graphically illustrates the optical density (OD) readings of bacteria in growth media (namely *E. Coli* in LB) achieved by two embodiments of the present invention flask reader compared to a spectrophotometer device.
Figure 20:
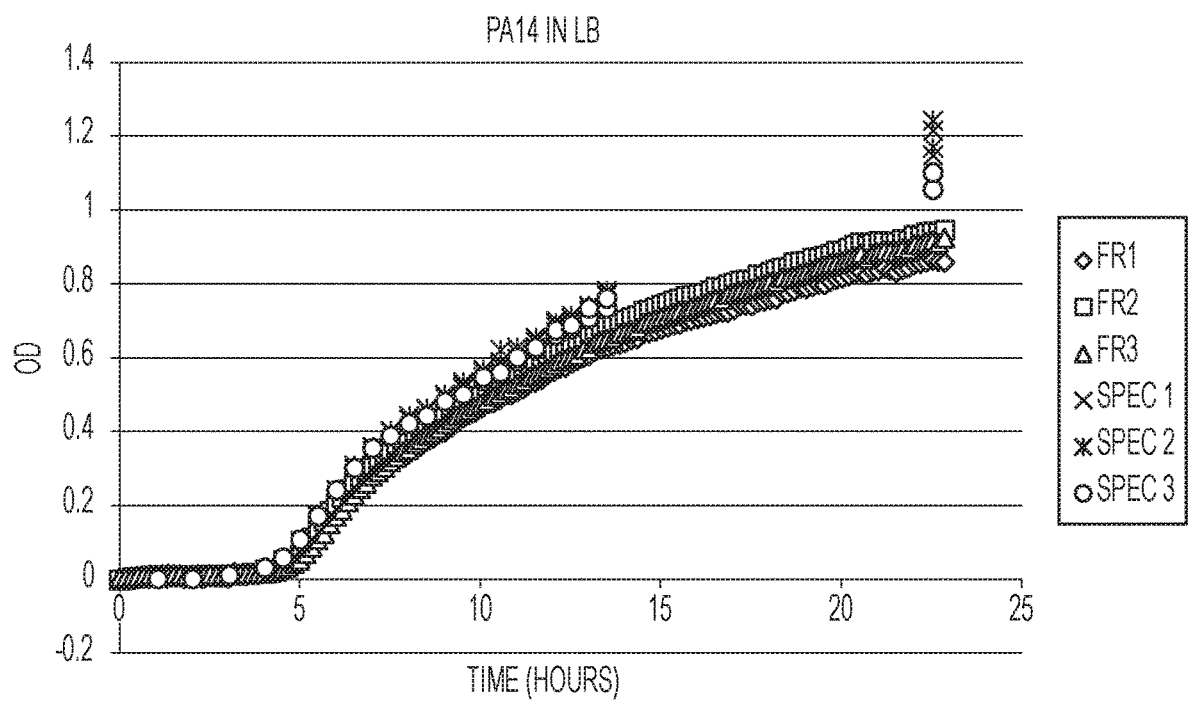
FIG. 20 graphically illustrates the optical density (OD) readings of bacteria in growth media (namely PA14 [*Pseudomonas Aeruginosa*] in LB) achieved by three embodiments of the present invention flask reader compared to a spectrophotometer device.
Figure 21:
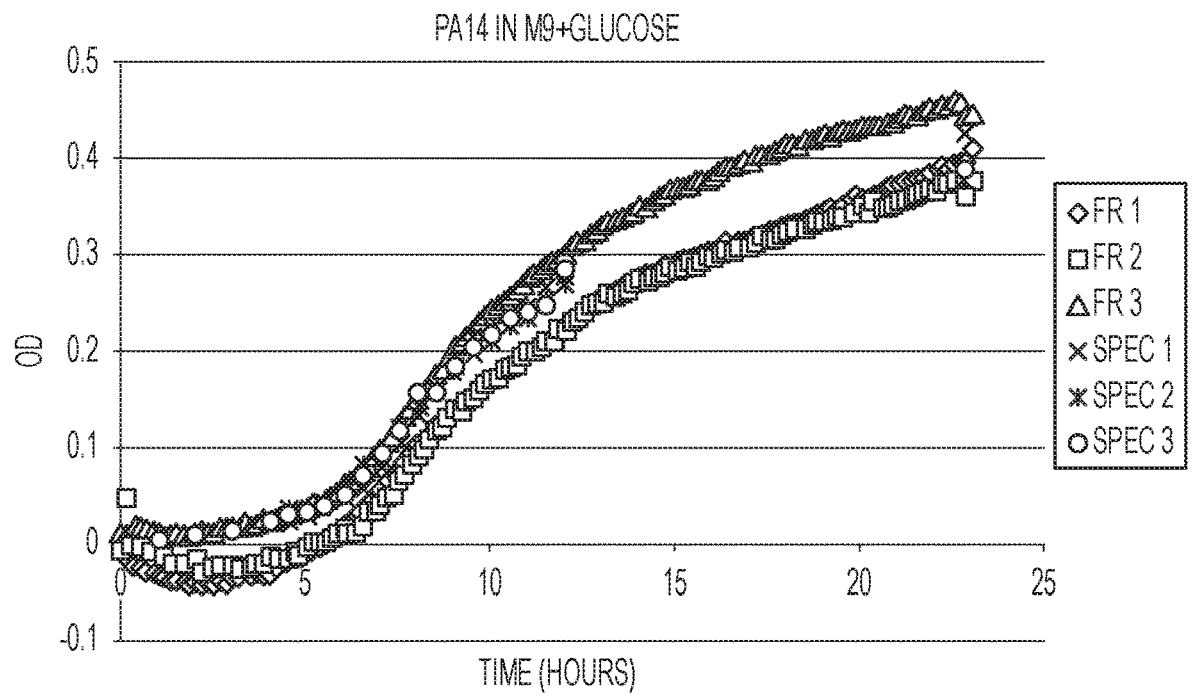
FIG. 21 graphically illustrates the optical density (OD) readings of bacteria in growth media (namely PA14 [*Pseudomonas Aeruginosa*] in M9+ glucose) achieved by three embodiments of the present invention flask reader compared to a spectrophotometer device.
Figure 22:
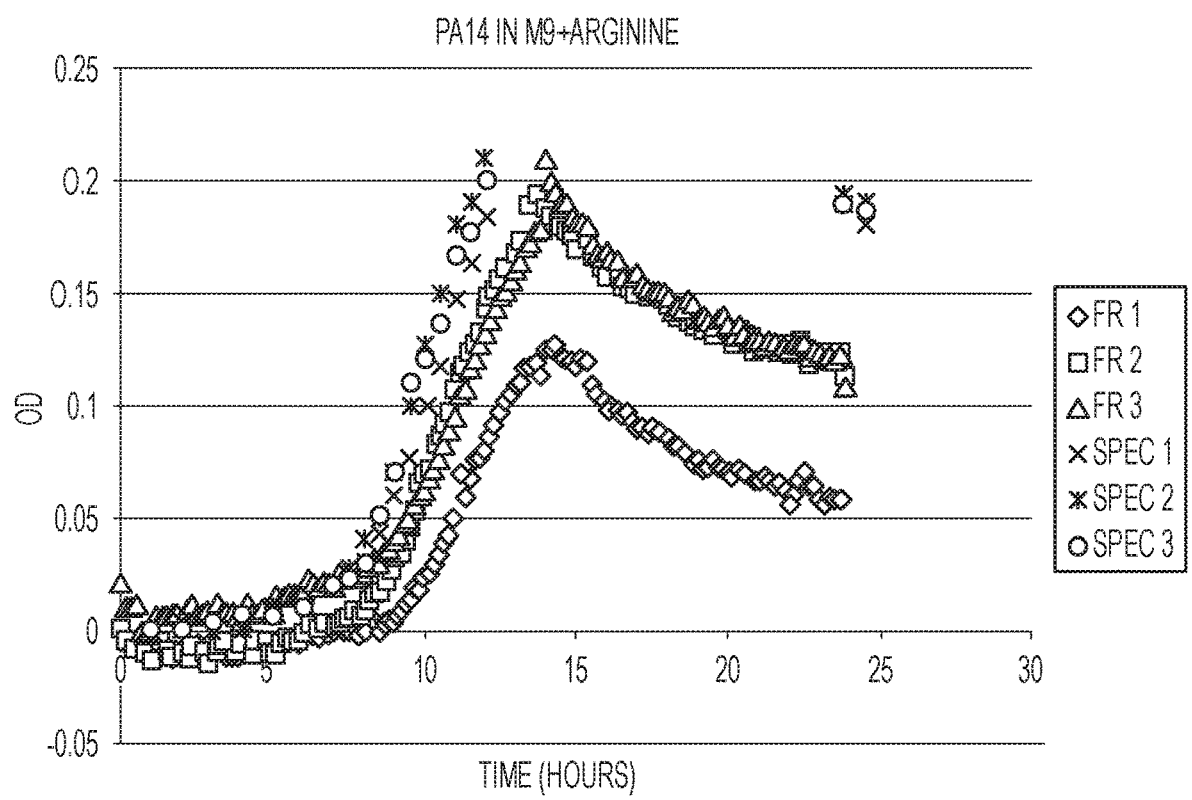
FIG. 22 graphically illustrates the optical density (OD) readings of bacteria in growth media (namely PA14 [*Pseudomonas Aeruginosa*] in M9+arginine) achieved by three embodiments of the present invention flask reader compared to a spectrophotometer device.

Turning to FIG. 18, FIG. 18 is a schematic block diagram for a system or related method of an embodiment of the present invention in whole or in part.

An embodiment of the optical density plate reader circuitry 60 provides an efficient approach to allow, for example, continuous reading of multiple receptor simultaneously. Each phototransistor 63 receptor was connected in series with a 100 resistor, and a potential difference of 5 volts was applied over each. A microcontroller 67 was used to measure the voltage across each resistor, with higher voltage indicating higher current passed through the phototransistor 63, which occurs under higher light exposure. In an embodiment, the microcontroller is, but is not limited thereto, the Arduino Mega 2560. 850 nm LEDs 61 and phototransistors 63 were used because of their availability, low cost, and demonstrated record in the Applicant's optical density plate reader.

To drive the LEDs, a TLC5916 constant-current driver 65 was used, and is capable of turning on up to eight LEDs 61 with an isolated 5-volt power supply. The final design used four LEDs 61, which can be switched independently to adjust total light reaching the bottom of the flask.

The modularity and interchangeability as disclosed herein may be accomplished with various mechanisms and approaches and should not be limited to any specific inner and outer connectivity relationship.

Any of the components or modules referred to with regards to any of the present invention embodiments of the device discussed herein, may be integrally or separately formed with one another. Further, redundant functions or structures of the components or modules may be implemented.

Any of the components or modules may be a variety of widths and lengths as desired or required for operational purposes.

It should be appreciated that various sizes, dimensions, contours, rigidity, shapes, flexibility and materials of any of the components or portions of components in the various embodiments of the device discussed throughout may be varied and utilized as desired or required. Similarly, locations and alignments of the various components may vary as desired or required. Moreover, modes and mechanisms for connectivity or interchangeability may vary.

It should be appreciated that the device and related components of the device discussed herein may take on all shapes along the entire continual geometric spectrum of manipulation of x, y and z planes to provide and meet the environmental, and structural demands and operational requirements. Moreover, locations, connections and alignments of the various components may vary as desired or required.

EXAMPLES

Practice of an aspect of an embodiment (or embodiments) of the invention will be still more fully understood from the following examples and experimental results, which are presented herein for illustration only and should not be construed as limiting the invention in any way.

Example No. 1

An embodiment of the optical density plate reader circuitry provides an efficient approach to allow, for example, continuous reading of multiple receptor simultaneously. Each phototransistor receptor was connected in series with a 100 kΩ resistor, and a potential difference of 5 volts was applied over each. An Arduino Mega 2560 was used to measure the voltage across each resistor, with higher voltage indicating higher current passed through the phototransistor, which occurs under higher light exposure. 850 nm LEDs and phototransistors were used because of their availability, low cost, and demonstrated record in the Applicant's optical density plate reader.

To drive the LEDs, a TLC5916 constant-current driver was used, and is capable of turning on up to eight LEDs with an isolated 5-volt power supply. The final design used four LEDs, which can be switched independently to adjust total light reaching the bottom of the flask.

Example No. 2

The final mechanical design (FIGS. 6, 7, and 9) ensures that the photodetector receptors will be centered under the flask, minimizes the base height, contains magnets to hold the parts of the stopper and base in place, minimizes the number and expense of parts which are not interchangeable between flask sizes, and includes a fluted version of the stopper for cultures requiring more aeration. The outer portion of the stopper and base would be unique to each flask size, but would have a constant inner dimension to allow a single disk of LEDs or photodetectors (as well as other electronic or hardware elements and components as desired or required) to fit into it. A functional device would have surface-mount LEDs and photodetectors, which would connect through metal contacts to the outer base and stopper. A cable would connect the LED wiring to the base, where another cable would route wires for both the photodetectors and LEDs to a central processing unit. A proprietary plug with minimal area and depth would connect the wires at each cable interface. The processing unit would ideally occupy the same area as a 50 mL flask, though it would be taller.

Experimental Results No. 1

To confirm that the device maintains linearity between milk concentration and OD, measurements were taken from a 500 mL flask filled with 100 mL of skim milk diluted with water, in varying ratios. Samples from 0 to 100% milk were used. The set of LEDs turned on and the shaking speed of the sample varied between experiments. To measure reproducibility of the readings, ten measurements were made at each milk concentration and compared to ten measurements taken in the Tecan plate reader.

The flask reader was shown to have very good linear performance, both stationary and during shaking at 180 RPM. It was demonstrated to track similarly to the Tecan plate reader, and variability (as measured by standard deviation among technical replicates) was extremely low, not much greater than the Tecan in the case of shaking, and lower than the Tecan when stationary. Furthermore, the expected decrease in linearity with increasing optical density was shown to occur at a similar rate to the Tecan, with all three methods maintaining linearity above $r^2=0.98$ until an $OD_{850}$ of about 1.2. Stationary measurement produced a higher OD-concentration slope compared to the shaking measurements.

Experimental Results No. 2

To further validate the flask reader, OD of a bacterial culture was measured over time using the flask reader as well as through individual samples measured in a standard spectrophotometer. An overnight $E.\ coli$ culture was diluted to an $OD_{600}$ of 0.05 and inoculated at a 1:100 ratio in lysogeny broth (LB) media. 100 mL of this diluted culture was placed in each of two 500 mL Erlenmeyer flasks. One of these cultures was outfitted with the flask reader and the other parallel culture had a standard rubber stopper. Both were placed in a 37° C. incubator shaking at 125 rpm. The flask reader measured OD of the culture in its flask upon inoculation and approximately every 10 minutes afterward. A 1 mL sample was taken from the parallel culture upon inoculation and every 30 minutes afterward in order to measure OD in a Tecan spectrophotometer at 600 and 850 nm. To replicate standard bacterial growth protocols with the spectrophotometer, samples with ODs beyond the linear range of the spectrophotometer were diluted, and the measured OD was multiplied by the dilution factor. The cultures were grown for 11.5 hours, at which point the growth curves were approaching stationary phase.

Measurements from the flask reader were linearly interpolated in MATLAB to estimate flask reader readings at times when samples were read by the Tecan. This interpolated data was used to calculate the linear correlation coefficient between Tecan and flask reader measurements.

OD of two parallel $E.\ coli$ cultures were measured at 850 nm with the flask reader and a Tecan plate reader over the course of 11.5 hours of growth. While this single dataset is not conclusive, and more data would be necessary to confirm performance, it is preliminarily very promising. The two types of measurements match very well for the lag and exponential phases of growth, and remain close after the exponential phase without any scaling. After linearly interpolating the flask reader data to match time points available in the Tecan data, the two sets of OD measurements showed strong linear correlation with each other, as expected; the two data sets had an $r^2$ value of 0.9647 across all time points, with especially strong correlation ($r^2=0.9868$) through the lag and exponential phase (through hour 5).

Experimental Results No. 3

The present inventors conducted other growth experiments in which data was taken over time from embodiments of the present invention flask reader device as well as a spectrophotometer device. For instance, the experimental setup was six flasks: three were read using the flask reader devices, and three had samples drawn out of them to be read in a single spectrophotometer. FIGS. 19-22 graphically represent the outcome of individual respective experiments. In these experiments, the present inventors studied growth of $E.\ Coli$ and $Pseudomonas\ Aeruginosa$ (PA14) in different growth media (LB, M9+arginine, or M9+glucose) in order to see how well an embodiment of the present invention flask reader device worked for, among other things, tracking different rates of growth of different organisms. The data demonstrates that an embodiment of the present invention flask reader device provided measurements that closely match the optical density (OD) readings taken by the spectrophotometer with little scaling needed in multiple experiments. Accordingly, these results demonstrate that an embodiment of the present invention device works well for, but is not limited thereto, multiple types of bacteria and growth rates.

Additional Examples

Example 1

A method for determining the optical density and/or change in optical density of a reaction mixture in an agitated vessel or container, the method comprising:
 a. passing radiation through the mixture from at least one electromagnetic emitter to at least one receptor;
 b. receiving the radiation passed through the reaction mixture with the at least one receptor;
 c. measuring the transmitted or scattered light detected by the at least one receptor;
 d. shaking the vessel or container and the reaction mixture during the measurement of the transmitted or scattered light;
 e. passing the raw measurement through a frequency filter of predetermined width to eliminate or reduce the effect of the frequency of the shaken reaction mixture; and
 f. analyzing the filtered data to provide the optical density and/or change in optical density of the reaction mixture.

Example 2

The method of example 1, wherein the detection of emitted radiation is effected at a frequency that is substantially greater than the frequency at which the vessel or container is shaken.

Example 3

The method of example 1 (as well as subject matter in whole or in part of example 2), wherein the frequency filter of predetermined width is a Gaussian moving average window filter.

Example 4

The method of example 3 (as well as subject matter in whole or in part of example 2), wherein the Gaussian moving average window length is approximately 5.6 seconds.

Example 5

The method of example 3 (as well as subject matter of one or more of any combination of examples 2 and 4), wherein the Gaussian moving average window length is approximately five periods at the lowest shaking speed of the vessel or container.

Example 6

The method of example 3 (as well as subject matter of one or more of any combination of examples 2 and 4-5), wherein the Gaussian moving average window length allows for approximately 800 measurements.

Example 7

The method of example 1 (as well as subject matter of one or more of any combination of examples 2-6), wherein the at least one emitter is configured to be in interchangeable association with the vessel or container.

Example 8

The method of example 1 (as well as subject matter of one or more of any combination of examples 2-7), wherein the at least one receptor is configured to be in interchangeable association with the vessel or container.

Example 9

The method of example 1 (as well as subject matter of one or more of any combination of examples 2-8), wherein passing radiation comprises positioning the at least one receptor externally to the bottom of the vessel or container wherein the vessel or container is substantially transparent to the radiation emitted by the at least one emitter.

Example 10

The method of example 9 (as well as subject matter of one or more of any combination of examples 2-8), wherein the at least one receptor is positioned proximal to or at the perimeter of the bottom of the vessel or container.

Example 11

The method of example 1 (as well as subject matter of one or more of any combination of examples 2-10), wherein the raw measurement from the of each of the at least the one receptors is individually passed through the frequency filter.

Example 12

The method of example 11 (as well as subject matter of one or more of any combination of examples 2-11), further comprising comparing the individual filtered applications to determine the eliminated or reduced effect for each of the at least one receptors.

Example 13

An apparatus for determining the optical density and/or change in optical density of a reaction mixture in an agitated vessel or container, the apparatus comprising:
   a. at least one electromagnetic emitter configured to pass radiation through the reaction mixture to at least one receptor, the at least one receptor configured to receive the transmitted or scattered light, while the reaction mixture is subjected to shaking;
   b. a processor configured to receive the transmitted or scattered light data, wherein the received data is passed through a frequency filter of predetermined width to eliminate or reduce the effect of the frequency at which the reaction mixture is shaken; and
   c. the processor configured to analyze the filtered data to provide the optical density and/or change in optical density of the reaction mixture.

Example 14

The apparatus of example 13, wherein the detection of emitted radiation is effected at a frequency that is substantially greater than the frequency of shaking at which the vessel or container is subjected.

Example 15

The apparatus of example 13 (as well as subject matter in whole or in part of example 14), wherein the frequency filter of predetermined width is a Gaussian moving average window filter.

Example 16

The apparatus of example 15 (as well as subject matter in whole or in part of example 14), wherein the Gaussian moving average window length is approximately 5.6 seconds.

Example 17

The apparatus of example 15 (as well as subject matter in whole or in part of example 14), wherein the Gaussian moving average window length is approximately five periods at the lowest shaking speed of the vessel or container.

Example 18

The apparatus of example 15 (as well as subject matter of one or more of any combination of examples 14 and 16-17), wherein the Gaussian moving average window length allows for approximately 800 measurements.

Example 19

The apparatus of example 13 (as well as subject matter of one or more of any combination of examples 14-18), wherein the at least one emitter is configured to be in interchangeable association with the vessel or container.

Example 20

The apparatus of example 19 (as well as subject matter of one or more of any combination of examples 14-18), further comprising a stopper, wherein the at least one emitter is disposed on the stopper, and the stopper is configured to provide the interchangeable association with the vessel or container.

Example 21

The apparatus of example 20 (as well as subject matter of one or more of any combination of examples 14-19), wherein the stopper is configured to provide the interchangeable association with the at least one emitter.

Example 22

The apparatus of example 19 (as well as subject matter of one or more of any combination of examples 14-21), further comprising a stopper, wherein the stopper comprises an inner stopper and an outer stopper, wherein the outer stopper is in communication with the vessel or container, and wherein:

the at least one emitter is disposed on the inner stopper, and the inner stopper is interchangeably disposed with the outer stopper

Example 23

The apparatus of example 22 (as well as subject matter of one or more of any combination of examples 14-21), wherein the disposal of the at least one emitter is provided by an emitter surface or emitter substrate.

Example 24

The apparatus of example 22 (as well as subject matter of one or more of any combination of examples 14-21 and 23), wherein the at least one emitter that is disposed on the inner stopper is interchangeably disposed with the inner stopper.

Example 25

The apparatus of example 24 (as well as subject matter of one or more of any combination of examples 14-23), wherein the disposal of the at least one emitter is provided by an emitter surface or emitter substrate.

Example 26

The apparatus of example 22 (as well as subject matter of one or more of any combination of examples 14-21 and 23-25), wherein the outer stopper in communication with the vessel or container is interchangeably disposed with the vessel or container.

Example 27

The apparatus of example 26 (as well as subject matter of one or more of any combination of examples 14-25), wherein the at least one emitter that is disposed on the inner stopper is interchangeably disposed with the inner stopper.

Example 28

The apparatus of example 27 (as well as subject matter of one or more of any combination of examples 14-26), wherein the disposal of the at least one emitter is provided by an emitter surface or emitter substrate.

Example 29

The apparatus of example 13 (as well as subject matter of one or more of any combination of examples 14-28), wherein the at least one receptor is configured to be in interchangeable association with the vessel or container.

Example 30

The apparatus of example 29 (as well as subject matter of one or more of any combination of examples 14-28), further comprising a base, wherein the at least one receptor is disposed on the base, and the base is configured to provide the interchangeable association with the vessel or container.

Example 31

The apparatus of example 30 (as well as subject matter of one or more of any combination of examples 14-29), wherein the base is configured to provide the interchangeable association with the at least one receptor.

Example 32

The apparatus of example 29 (as well as subject matter of one or more of any combination of examples 14-28 and 30-31), further comprising a base, wherein the base comprises an inner base and an outer base, wherein the outer base is in communication with the vessel or container, and wherein:

the at least one receptor is disposed on the inner base, and the inner base is interchangeably disposed with the outer base.

Example 33

The apparatus of example 32, wherein the at least one receptor that is disposed on the inner base is interchangeably disposed with the inner base.

Example 34

The apparatus of example 32 (as well as subject matter of one or more of any combination of examples 14-31 and 33), wherein the outer base in communication with the vessel or container is interchangeably disposed with the vessel or container.

Example 35

The apparatus of example 34 (as well as subject matter of one or more of any combination of examples 14-33), wherein the at least one receptor that is disposed on the inner base is interchangeably disposed with the inner base.

Example 36

The apparatus of example 13 (as well as subject matter of one or more of any combination of examples 14-35), wherein the vessel or container has a bottom, and wherein the at least one receptor is positioned externally to the bottom of the vessel or container.

Example 37

The apparatus of example 36 (as well as subject matter of one or more of any combination of examples 14-35), wherein the at least one receptor is positioned proximal to or at the perimeter of the bottom of the vessel or container.

Example 38

The apparatus of example 13 (as well as subject matter of one or more of any combination of examples 14-37), further comprising:

a vessel or container configured to hold the reaction mixture

Example 39

The apparatus of example 38 (as well as subject matter of one or more of any combination of examples 14-37), wherein the vessel or container is substantially transparent to the radiation emitted by the at least one electromagnetic emitter.

Example 40

The apparatus of example 13 (as well as subject matter of one or more of any combination of examples 14-39), wherein each electromagnetic emitter comprises a light emitting diode.

Example 41

The apparatus of example 40 (as well as subject matter of one or more of any combination of examples 14-39), wherein each light emitting diode is configured to emit infrared light.

Example 42

The apparatus of example 41 (as well as subject matter of one or more of any combination of examples 14-40), wherein each infrared light emitting diode comprises a peak emission between 700 nm and 1000 nm.

Example 43

The apparatus of example 40 (as well as subject matter of one or more of any combination of examples 14-39 and 41-42), wherein each light emitting diode is configured to emit visible light.

Example 44

The apparatus of example 43 (as well as subject matter of one or more of any combination of examples 14-42), wherein each visible light emitting diode comprises a peak emission between 400 nm and 700 nm.

Example 45

The apparatus of example 13 (as well as subject matter of one or more of any combination of examples 14-44), wherein each receptor comprises a phototransistor detector measuring an actual intensity of radiation received from at least one of the light emitting diodes.

Example 46

The apparatus of example 13 (as well as subject matter of one or more of any combination of examples 14-45), wherein processor is configured whereby the frequency filter is applied individually to the received data from each of the at least the one receptors.

Example 47

The apparatus of example 46 (as well as subject matter of one or more of any combination of examples 14-45), wherein processor is configured to compare the individual filtered applications to determine the eliminated or reduced effect for each of the at least one receptors.

Example 48

An apparatus for determining the optical density and/or change in optical density of a reaction mixture in an agitated vessel or container, the apparatus comprising:
at least one electromagnetic emitter configured to pass radiation through the reaction mixture to at least one receptor, the at least one receptor configured to receive the transmitted or scattered light, while the reaction mixture is subjected to shaking; wherein:
  a. the at least one emitter is configured to be in interchangeable association with the vessel or container;
  b. the at least one receptor is configured to be in interchangeable association with the vessel or container; or
  c. the at least one emitter is configured to be in interchangeable association with the vessel or container, and the at least one receptor is configured to be in interchangeable association with the vessel or container;
a processor configured to receive the transmitted or scattered light data and filter to eliminate or reduce the effect of the frequency at which the reaction mixture is shaken; and
the processor configured to analyze the filtered data to provide the optical density and/or change in optical density of the reaction mixture.

Example 49

The apparatus of example 48 (as well as subject matter in whole or in part of example 77), further comprising a stopper, wherein the at least one emitter is disposed on the stopper, and the stopper is configured to provide the interchangeable association with the vessel or container.

Example 50

The apparatus of example 49 (as well as subject matter in whole or in part of example 77), wherein the stopper is configured to provide the interchangeable association with the at least one emitter.

Example 51

The apparatus of example 48 (as well as subject matter of one or more of any combination of examples 49-50 and 77), further comprising a stopper, wherein the stopper comprises an inner stopper and an outer stopper, wherein the outer stopper is in communication with the vessel or container, and wherein:
the at least one emitter is disposed on the inner stopper, and
the inner stopper is interchangeably disposed with the outer stopper.

Example 52

The apparatus of example 51 (as well as subject matter of one or more of any combination of examples 49-50 and 77), wherein the disposal of the at least one emitter is provided by an emitter surface or emitter substrate.

Example 53

The apparatus of example 51 (as well as subject matter of one or more of any combination of examples 49-50 and 77), wherein the at least one emitter that is disposed on the inner stopper is interchangeably disposed with the inner stopper.

Example 54

The apparatus of example 53 (as well as subject matter of one or more of any combination of examples 49-52 and 77), wherein the disposal of the at least one emitter is provided by an emitter surface or emitter substrate.

Example 55

The apparatus of example 51 (as well as subject matter of one or more of any combination of examples 49-50 and 77), wherein the outer stopper in communication with the vessel or container is interchangeably disposed with the vessel or container.

Example 56

The apparatus of example 55 (as well as subject matter of one or more of any combination of examples 49-54 and 77), wherein the at least one emitter that is disposed on the inner stopper is interchangeably disposed with the inner stopper.

Example 57

The apparatus of example 56 (as well as subject matter of one or more of any combination of examples 49-55 and 77), wherein the disposal of the at least one emitter is provided by an emitter surface or emitter substrate.

Example 58

The apparatus of example 48 (as well as subject matter of one or more of any combination of examples 49-57 and 77), further comprising a base, wherein the at least one receptor is disposed on the base, and the base is configured to provide the interchangeable association with the vessel or container.

Example 59

The apparatus of example 58 (as well as subject matter of one or more of any combination of examples 49-57 and 77), wherein the base is configured to provide the interchangeable association with the at least one receptor.

Example 60

The apparatus of example 48 (as well as subject matter of one or more of any combination of examples 49-59 and 77), further comprising a base, wherein the base comprises an inner base and an outer base, wherein the outer base is in communication with the vessel or container, and wherein:
the at least one receptor is disposed on the inner base, and
the inner base is interchangeably disposed with the outer base.

Example 61

The apparatus of example 60 (as well as subject matter of one or more of any combination of examples 49-59 and 77), wherein the at least one receptor that is disposed on the inner base is interchangeably disposed with the inner base.

Example 62

The apparatus of example 60 (as well as subject matter of one or more of any combination of examples 49-59, 61, and 77), wherein the outer base in communication with the vessel or container is interchangeably disposed with the vessel or container.

Example 63

The apparatus of example 62 (as well as subject matter of one or more of any combination of examples 49-61 and 77), wherein the at least one receptor that is disposed on the inner base is interchangeably disposed with the inner base.

Example 64

The apparatus of example 48 (as well as subject matter of one or more of any combination of examples 49-63 and 77), wherein the vessel or container has a bottom, and wherein the at least one receptor is positioned externally to the bottom of the vessel or container.

Example 65

The apparatus of example 64 (as well as subject matter of one or more of any combination of examples 49-63 and 77), wherein the at least one receptor is positioned proximal to or at the perimeter of the bottom of the vessel or container.

Example 66

The apparatus of example 48 (as well as subject matter of one or more of any combination of examples 49-65 and 77), further comprising:
a vessel or container configured to hold the reaction mixture

Example 67

The apparatus of example 66 (as well as subject matter of one or more of any combination of examples 49-65 and 77), wherein the vessel or container is substantially transparent to the radiation emitted by the at least one electromagnetic emitter.

Example 68

The apparatus of example 48 (as well as subject matter of one or more of any combination of examples 49-67 and 77), wherein each electromagnetic emitter comprises a light emitting diode.

Example 69

The apparatus of example 68 (as well as subject matter of one or more of any combination of examples 49-67 and 77), wherein each light emitting diode is configured to emit infrared light.

Example 70

The apparatus of example 69 (as well as subject matter of one or more of any combination of examples 49-68 and 77), wherein each infrared light emitting diode comprises a peak emission between 700 nm and 1000 nm.

Example 71

The apparatus of example 68 (as well as subject matter of one or more of any combination of examples 49-67, 69-70, and 77), wherein each light emitting diode is configured to emit visible light.

Example 72

The apparatus of example 71 (as well as subject matter of one or more of any combination of examples 49-70 and 77), wherein each visible light emitting diode comprises a peak emission between 400 nm and 700 nm.

Example 73

The apparatus of example 48 (as well as subject matter of one or more of any combination of examples 49-72 and 77), wherein each receptor comprises a phototransistor detector measuring an actual intensity of radiation received from at least one of the light emitting diodes.

Example 74

The apparatus of example 48 (as well as subject matter of one or more of any combination of examples 49-73 and 77), wherein processor is configured whereby the frequency filter is applied individually to the received data from each of the at least the one receptors.

Example 75

The apparatus of example 74 (as well as subject matter of one or more of any combination of examples 49-73 and 77), wherein processor is configured to compare the individual filtered applications to determine the eliminated or reduced effect for each of the at least one receptors.

Example 76

The apparatus of example 48 (as well as subject matter of one or more of any combination of examples 49-75 and 77), wherein the filtering comprises extracting the transmitted light intensity from the received transmitted or scattered light data.

Example 77

An apparatus for determining the optical density and/or change in optical density of a reaction mixture in an agitated vessel or container, the apparatus comprising:
  at least one electromagnetic emitter configured to pass radiation through the reaction mixture to at least one receptor, the at least one receptor configured to receive the transmitted or scattered light, while the reaction mixture is subjected to shaking; wherein:
    a. the at least one emitter is configured to be interchangeable association with the vessel or container;
    b. the at least one receptor is configured to be interchangeable association with the vessel or container; or
    c. the at least one emitter is configured to be in interchangeable association with the vessel or container, and the at least one receptor is configured to be in interchangeable association with the vessel or container;
  a processor configured to receive the transmitted or scattered light data; and the processor configured to analyze the filtered data to provide the optical density and/or change in optical density of the reaction mixture.

Example 78

The method of example 1 (as well as subject matter of one or more of any combination of examples 2-13), wherein the determining the optical density and/or change in optical density of a reaction mixture is performed continuously and in real time.

Example 79

The apparatus of anyone of examples 13, 48, and 77 (as well as subject matter of one or more of any combination of examples 14-47 and 49-76), wherein the determining the optical density and/or change in optical density of a reaction mixture is performed continuously and in real time.

Example 80

The method of using any of the apparatuses (systems or devices) or their components or structures (in whole or in part) provided in any one or more of examples 13-77 and 79.

Example 81

The method of manufacturing any of the apparatuses (systems or devices) or their components or structures (in whole or in part) provided in any one or more of examples 13-77 and 79.

REFERENCES

The devices, systems, apparatuses, materials, components, computer readable medium, algorithms, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section):
1. U.S. Pat. No. 8,603,772 B2, Debreczeny, M., et al., "Particle Sensor with Wide Linear Range", Dec. 10, 2013.
2. U.S. Pat. No. 8,405,033 B2, Debreczeny, M., et al., "Optical Sensor for Rapid Determination of Particulate Concentration", Mar. 26, 2013.
3. U.S. Pat. No. 7,339,671 B2, Peng, H., "Apparatus and Method for Monitoring Biological Cell Culture", Mar. 4, 2008.
4. International Patent Application Publication No. DE 102014001284 B3, Herzog, et al., "Method, Apparatus and System for Automated Determination of Optical Densities or the Change of Optical Densities of Reaction Mixtures in Shaken Reactors", Jan. 22, 2015.
5. International Patent Application Publication No. WO 2015/114083 A1, Herzog, et al., "Method, Device and System for the Automated Determination of Optical Densities or of the Change in Optical Densities of Reaction Mixtures in Shaken Reactors", Aug. 6, 2015.
6. U.S. Patent Application Publication No. US 2015/0260642 A1, Papin, et al., "Miniaturized Multiwell Plate Reader for Phenotypic Screening", Sep. 17, 2015.
7. International Patent Application No. WO 2014/058869 A1, Papin, et al., "Miniaturized Multiwell Plate Reader for Phenotypic Screening", Apr. 17, 2014.

8. International Patent Application Publication No. DE 102014001284 B3, Herzog, et al., "Method, Apparatus and System for Automated Determination of Optical Densities or the Change of Optical Densities of Reaction Mixtures in Shaken Reactors", Jan. 22, 2015, Google English Translation.
9. Copeland, D. (2014). Original Market Research, in collaboration with the Papin laboratory. *Emerge Life Sciences*.
10. Cox, R. P., Miller, M., Bang Nielsen, J., Nielsen, M., & Kirk Thomsen, J. (1989). Continuous turbidometric measurements of microbial cell density in bioreactors using a light-emitting diode and a photodiode. *Journal of Microbiological Methods*, 10(1), 25-31.
11. Debreczeny, Martin P., Romero, Jaime, & Petersen, Ethan. Particle sensor with wide linear range. Buglab Llc, assignee. U.S. Pat. No. 8,603,772 B2. 10 Dec. 2013.
12. Dougherty, B. V. (2014, July 10). Customer interviews (anonymized market research).
13. Jensen, P. A., Dougherty, B. V., Moutinho, T. J., & Papin, J. A. (2014, Nov. 3). Miniaturized plate readers for low-cost, high-throughput phenotypic screening. *Journal of Laboratory Automation*, 19(6).
14. Monod, J, (1949). The growth of bacterial cultures, *Annual Reviews in Microbiology*, 3(1), 371-394.
15. Myers, J. A., Curtis, B. S., & Curtis, W. R. (2013). Improving accuracy of cell and chromophore concentration measurements using optical density. *BMC biophysics*, 6(1), 4.
16, PreSens (2015). SFR (Shake Flask Reader). *Products: Systems*. PreSens Precision Sensing GmbH. http://www.presens.de/
17. Sivashanmugam, A., Murray, V., Cui, C., Zhang, Y., Wang, J., & Li, Q. (2009). Practical protocols for production of very high yields of recombinant proteins using *Escherichia coli*. *Protein Science*, 18(5), 936-938.
18. Toprak, E., Veres, A., Yildiz, S., Pedraza, J. M., Chait, R., Paulsson, J., & Kishony, R. (2013). Building a morbidostat: an automated continuous-culture device for studying bacterial drug resistance under dynamically sustained drug inhibition. *Nature protocols*, 8(3), 555-567.
19. Udekwu, K. I., Parrish, N., Ankomah, P. Baquero, F., & Levin. B. R. (2009). Functional relationship between bacterial cell density and the efficacy of antibiotics. *Journal of Antimicrobial Chemotherapy*, 63(4), 74.5-757.
20. Underwood, S. A., Buszko, M. L., Shanmugam, K. T. & Ingram, L. O. (2004). Lack of protective osmolytes limits final cell density and volumetric productivity of ethanologenic *Escherichia coli* KO11 during xylose fermentation. *Applied and Environmental Microbiology*, 70(5), 2734-2740.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A method for determining the optical density and/or change in optical density of a reaction mixture in an agitated vessel or container, said method comprising:
    passing radiation through the mixture from at least one electromagnetic emitter to at least one receptor;
    receiving the radiation passed through the reaction mixture with said at least one receptor;
    measuring the transmitted or scattered light detected by said at least one receptor;
    shaking said vessel or container and said reaction mixture during said measurement of the transmitted or scattered light;
    individually passing the raw measurement from each of said at least one receptors through a frequency filter of predetermined width to eliminate or reduce the effect of the frequency of the shaken reaction mixture; and analyzing the filtered data to provide the optical density and/or change in optical density of said reaction mixture.

2. The method of claim 1, wherein the detection of emitted radiation is effected at a frequency that is substantially greater than the frequency at which said vessel or container is shaken.

3. The method of claim 1, wherein said frequency filter of predetermined width is a Gaussian moving average window filter.

4. The method of claim 3, wherein the Gaussian moving average window length is approximately 5.6 seconds.

5. The method of claim 3, wherein the Gaussian moving average window length is approximately five periods at the lowest shaking speed of the vessel or container.

6. The method of claim 3, wherein the Gaussian moving average window length allows for approximately 800 measurements.

7. The method of claim 1, wherein said at least one emitter is configured to be in interchangeable association with said vessel or container.

8. The method of claim 1, wherein said at least one receptor is configured to be in interchangeable association with said vessel or container.

9. The method of claim 1, wherein passing radiation comprises positioning said at least one receptor externally to the bottom of said vessel or container wherein the vessel or container is substantially transparent to the radiation emitted by said at least one emitter.

10. The method of claim 9, wherein said at least one receptor is positioned proximal to or at the perimeter of the bottom of said vessel or container.

11. The method of claim 1, further comprising comparing said individual filtered applications to determine the eliminated or reduced effect for each of said at least one receptors.

12. An apparatus for determining the optical density and/or change in optical density of a reaction mixture in an agitated vessel or container, said apparatus comprising:
at least one electromagnetic emitter configured to pass radiation through the reaction mixture to at least one receptor, said at least one receptor configured to receive the transmitted or scattered light, while the reaction mixture is subjected to shaking;
a processor configured to receive the transmitted or scattered light data, wherein said received data from each of said at least one receptor is individually passed through a frequency filter of predetermined width to eliminate or reduce the effect of the frequency at which the reaction mixture is shaken; and
said processor configured to analyze the filtered data to provide the optical density and/or change in optical density of said reaction mixture.

13. The apparatus of claim 12, wherein the detection of emitted radiation is effected at a frequency that is substantially greater than the frequency of shaking at which said vessel or container is subjected.

14. The apparatus of claim 12, wherein said frequency filter of predetermined width is a Gaussian moving average window filter.

15. The apparatus of claim 14, wherein the Gaussian moving average window length is approximately 5.6 seconds.

16. The apparatus of claim 14, wherein the Gaussian moving average window length is approximately five periods at the lowest shaking speed of the vessel or container.

17. The apparatus of claim 14, wherein the Gaussian moving average window length allows for approximately 800 measurements.

18. The apparatus of claim 12, wherein said at least one emitter is configured to be in interchangeable association with said vessel or container.

19. The apparatus of claim 18, further comprising a stopper, wherein said at least one emitter is disposed on said stopper, and said stopper is configured to provide the interchangeable association with said vessel or container.

20. The apparatus of claim 19, wherein said stopper is configured to provide the interchangeable association with said at least one emitter.

21. The apparatus of claim 18, further comprising a stopper, wherein said stopper comprises an inner stopper and an outer stopper, wherein said outer stopper is in communication with said vessel or container, and wherein:
said at least one emitter is disposed on said inner stopper, and
said inner stopper is interchangeably disposed with said outer stopper.

22. The apparatus of claim 21, wherein said disposal of said at least one emitter is provided by an emitter surface or emitter substrate.

23. The apparatus of claim 21, wherein said at least one emitter that is disposed on said inner stopper is interchangeably disposed with said inner stopper.

24. The apparatus of claim 23, wherein said disposal of said at least one emitter is provided by an emitter surface or emitter substrate.

25. The apparatus of claim 21, wherein said outer stopper in communication with said vessel or container is interchangeably disposed with said vessel or container.

26. The apparatus of claim 25, wherein said at least one emitter that is disposed on said inner stopper is interchangeably disposed with said inner stopper.

27. The apparatus of claim 26, wherein said disposal of said at least one emitter is provided by an emitter surface or emitter substrate.

28. The apparatus of claim 12, wherein said at least one receptor is configured to be in interchangeable association with said vessel or container.

29. The apparatus of claim 28, further comprising a base, wherein said at least one receptor is disposed on said base, and said base is configured to provide the interchangeable association with said vessel or container.

30. The apparatus of claim 29, wherein said base is configured to provide the interchangeable association with said at least one receptor.

31. The apparatus of claim 28, further comprising a base, wherein said base comprises an inner base and an outer base, wherein said outer base is in communication with said vessel or container, and wherein:
said at least one receptor is disposed on said inner base, and
said inner base is interchangeably disposed with said outer base.

32. The apparatus of claim 31, wherein said at least one receptor that is disposed on said inner base is interchangeably disposed with said inner base.

33. The apparatus of claim 31, wherein said outer base in communication with said vessel or container is interchangeably disposed with said vessel or container.

34. The apparatus of claim 33, wherein said at least one receptor that is disposed on said inner base is interchangeably disposed with said inner base.

35. The apparatus of claim 12, wherein said vessel or container has a bottom, and wherein said at least one receptor is positioned externally to the bottom of said vessel or container.

36. The apparatus of claim 35, wherein said at least one receptor is positioned proximal to or at the perimeter of the bottom of said vessel or container.

37. The apparatus of claim 12, further comprising:
a vessel or container configured to hold the reaction mixture.

38. The apparatus of claim 37, wherein the vessel or container is substantially transparent to the radiation emitted by said at least one electromagnetic emitter.

39. The apparatus of claim 12, wherein each electromagnetic emitter comprises a light emitting diode.

40. The apparatus of claim 39, wherein each light emitting diode is configured to emit infrared light.

41. The apparatus of claim 40, wherein each infrared light emitting diode comprises a peak emission between 700 nm and 1000 nm.

42. The apparatus of claim 39, wherein each light emitting diode is configured to emit visible light.

43. The apparatus of claim 42, wherein each visible light emitting diode comprises a peak emission between 400 nm and 700 nm.

44. The apparatus of claim 12, wherein each receptor comprises a phototransistor detector measuring an actual intensity of radiation received from at least one of said light emitting diodes.

45. The apparatus of claim 12, wherein said processor is configured to compare said individual filtered applications to determine the eliminated or reduced effect for each of said at least one receptors.

46. The method of claim 1, wherein said determining the optical density and/or change in optical density of a reaction mixture is performed continuously and in real time.

47. The apparatus of claim 12, wherein said determining the optical density and/or change in optical density of a reaction mixture is performed continuously and in real time.

* * * * *